United States Patent
Scotto

(10) Patent No.: US 10,202,336 B2
(45) Date of Patent: Feb. 12, 2019

(54) PLANT FOR UREA PRODUCTION

(71) Applicant: Casale SA, Lugano (CH)

(72) Inventor: Andrea Scotto, Breganzona (CH)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 15/527,166

(22) PCT Filed: Oct. 9, 2015

(86) PCT No.: PCT/EP2015/073379
§ 371 (c)(1),
(2) Date: May 16, 2017

(87) PCT Pub. No.: WO2016/083005
PCT Pub. Date: Jun. 2, 2016

(65) Prior Publication Data
US 2017/0362169 A1 Dec. 21, 2017

(30) Foreign Application Priority Data
Nov. 26, 2014 (EP) .................................. 14194856

(51) Int. Cl.
*C07C 273/04* (2006.01)
*B01J 19/00* (2006.01)

(52) U.S. Cl.
CPC .......... *C07C 273/04* (2013.01); *B01J 19/0013* (2013.01); *B01J 2219/00006* (2013.01); *B01J 2219/00024* (2013.01); *B01J 2219/00074* (2013.01); *Y02P 20/123* (2015.11)

(58) Field of Classification Search
CPC ................ B01J 19/0006; B01J 19/0013; B01J 19/2465; B01J 2219/00024; B01J 2219/00006; B01J 2219/00074; B01J 2219/00162; C07C 273/04
See application file for complete search history.

(56) References Cited

U.S. PATENT DOCUMENTS

2015/0343369 A1* 12/2015 Kojima .............. B01D 53/1475
423/228

FOREIGN PATENT DOCUMENTS

| GB | 2 146 632 A | 4/1985 |
| WO | 2014/001917 A2 | 1/2014 |

OTHER PUBLICATIONS

International Search Report issued in connection with PCT/EP2015/073379.
International Preliminary Report on Patentability issued in connection with PCT/EP2015/073379.
Sharma et al., "Parametric Evaluation of Heat Recovery Steam Generator (HRSG)", Heat Transfer-Asian Research, Dec. 13, 2013, vol. 43, No. 8, pp. 691-705.

* cited by examiner

*Primary Examiner* — Lessanework Seifu
(74) *Attorney, Agent, or Firm* — Akerman LLP

(57) ABSTRACT

Plant for the synthesis of urea, comprising: a synthesis section comprising at least one reactor, a compressor for supplying $CO_2$ to said synthesis section, a gas turbine for the operation of said $CO_2$ compressor and a heat recovery steam generator; the heat source of said heat recovery steam generator consists of the exhaust gases of said gas turbine, and at least one steam flow produced by said heat recovery steam generator is used as heat source for at least one component of said urea plant.

10 Claims, 1 Drawing Sheet

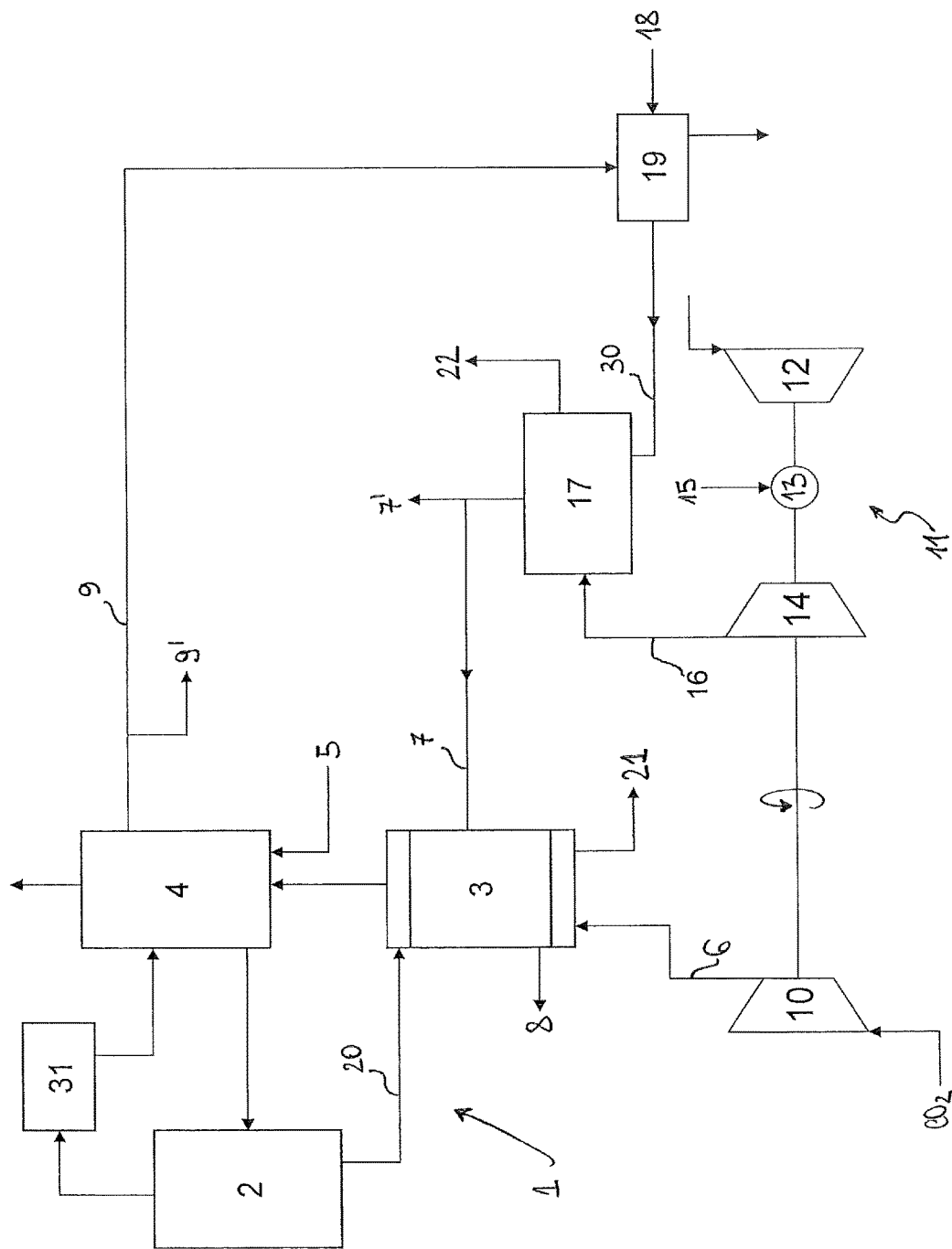

PLANT FOR UREA PRODUCTION

This application is a national phase of PCT/EP2012/073379, filed Oct. 9, 2015, and claims priority to EP 14194856.2, filed Nov. 26, 2014, the entire contents of both of which are hereby incorporated by reference

FIELD OF APPLICATION

The invention relates to the field of plants for the synthesis of urea from ammonia and carbon dioxide.

PRIOR ART

Urea is produced by reaction between ammonia and carbon dioxide ($CO_2$) at high pressure. The known methods for urea synthesis are described in literature, for example in Ullmann's Encyclopedia of Industrial Chemistry, Wiley-VCH Verlag, vol. A27.

A urea synthesis plant usually comprises a high-pressure synthesis section, and said section includes a reactor, a high-pressure stripper and a high-pressure condenser. The reactor produces an aqueous solution comprising urea and unreacted ammonium carbamate, which is supplied to the stripper. The stripper produces a solution of urea and a gaseous phase mainly containing unreacted ammonia and $CO_2$, which is condensed and recycled to the reactor. The stripping process may be carried out in the presence of a stripping agent, typically fresh $CO_2$ or ammonia. The plants which use $CO_2$ as stripping agent are known as $CO_2$-stripping plants.

The carbon dioxide is supplied at high pressure to the stripper and/or to the reactor, depending on the type of plant. In any case, a $CO_2$ compressor able to raise the pressure of the $CO_2$ to the level of the synthesis section, typically to above 100 bar, is required. Said $CO_2$ compressor constitutes one of the main energy users of the plant.

In the prior art, said $CO_2$ compressor is operated directly by a steam turbine or an electric motor.

A plant for the urea production, in fact, comprises a complex steam system with several steam levels, including steam generators and steam users. Steam is generally produced during the stages which require removal of heat from a process fluid, at a pressure level which depends on the temperature of the available heat; steam may be used both for process purposes and for producing mechanical work for operation of the machines.

For example, the stripper of the synthesis section, referred to above, is a steam user since the stripping process must provide heat to the solution comprising urea and carbamate. Typically the stripper is a shell and tube exchanger, in which the solution is supplied inside the tubes, and the tube bundle is heated externally by steam at about 20 bar. Therefore, the high-pressure stripper constitutes an important energy user (energy being in the form of heat). The carbamate condenser instead produces steam, since the condensation heat is typically released to evaporating water. The pressure of the steam which can be obtained from the condenser, however, is generally low (for example 3 bar).

In order to produce mechanical work, one or more steam turbines are used. A steam turbine may drive directly a machine (for example a compressor or a pump), or may drive an electric generator; the energy thus obtained may be used by the machines of the plant.

In some cases, the steam generated internally is not sufficient to meet all the requirements of the plant. The shortage of steam may be offset, for example, by importing steam from the outside or by introducing an auxiliary steam generator. However, external steam is not always available and an auxiliary generator consumes fuel and increases the costs.

In the light of the above, it can be understood that the optimization of the steam system and its integration with the remainder of the plant are particularly important for reducing energy consumption, namely for increasing the urea production per unit of energy used. One of the problems consists in conveniently using the steam depending on the energy level at which it is available. For example, one of the problems consists in finding a convenient use for the steam with a low temperature level and/or low pressure, since it may contain a significant amount of heat, which, however, cannot be easily exploited. In the prior art continuous efforts are being made to improve this aspect of the urea plants.

SUMMARY OF THE INVENTION

The invention aims at improving the energy efficiency of the plants for the high-pressure synthesis of urea from ammonia and carbon dioxide, in particular at reducing the consumption of the compressor needed to raise the carbon dioxide to the synthesis pressure, and at optimizing the integration between the process and the respective steam system.

These objects are achieved with a plant according to the claims.

A plant for the synthesis of urea according to the invention comprises a synthesis section which includes at least one reactor for the synthesis of urea and comprises a $CO_2$ compressor for supplying $CO_2$ to the synthesis section; the plant is characterized in that it comprises a gas turbine for the operation of said $CO_2$ compressor, and in that it comprises a heat recovery steam generator, wherein the heat source of said heat recovery steam generator consists of the exhaust gases of said gas turbine and wherein a steam flow produced by said heat recovery steam generator is used as process steam in said plant.

Preferably, the synthesis section comprises at least one reactor, a stripper and a condenser. In this case the synthesis section is typically referred to as a "synthesis loop".

The preferred features are described in the dependent claims.

The idea forming the basis of the invention is to operate said $CO_2$ compressor using a gas turbine. Said gas turbine consumes a fuel, but has the great advantage of releasing hot gases which can be exploited in a heat recovery steam generator (HRSG). Said generator produces steam which can be used for the process, and more preferably for supplying heat to the high-pressure stripper of said plant.

More advantageously, the steam produced in the heat recovery steam generator is obtained by means of evaporation of a demineralized water flow. The demineralization treatment is performed more preferably in a degasser which uses, as heat source, steam supplied by cooling of the carbamate condenser of the synthesis section. Said heating steam of the degasser is typically at a low pressure, for example less than 5 bar and typically around 3 bar. The water demineralization treatment is performed for example at about 100-120° C.

The gas turbine may operate the $CO_2$ compressor directly or indirectly. Preferably, the gas turbine drives directly said compressor, for example the turbine shaft is mechanically connected to the compressor shaft.

The invention offers the advantage of an improved integration between the process and the respective steam system, and an efficient use of the energy.

The mechanical power produced by the gas turbine, which constitutes valuable energy, is used directly to operate the compressor, which forms one of the main energy consumers of the plant.

The heat recovered from the exhaust gases of the turbine is used to supply heat to the stripper. As a consequence, the fuel of the gas turbine is basically exploited twice. The applicant has found that the temperature of the exhaust gases of a conventional gas turbine (typically about 400-500° C.) allows steam to be generated under optimum conditions for the synthesis-loop stripper. Therefore, one of the advantages of the invention is that the fuel of the gas turbine is sufficient to meet the needs of two of the main energy consumers of the plant, namely the $CO_2$ compressor (which requires mechanical energy) and the stripper (which requires thermal energy).

According to a further aspect of the invention, the water supplied to the recovery generator, in order to generate steam for the stripper, undergoes degassing with steam at a low pressure, for example 3 bar. This low-heat steam is advantageously recycled by the carbamate condenser. Consequently the invention provides an effective method for using the low-pressure steam supplied by the carbamate condenser. This steam is in fact used to degas the water of the heat recovery steam generator, and in this it way contributes to the production of steam at a higher pressure.

The invention also relates to a method for revamping a plant for the synthesis of urea from ammonia and $CO_2$ according to the accompanying claims.

The method of revamping is characterized by the additional installation of a gas turbine for the operation of said $CO_2$ compressor, and by the additional installation of a heat recovery steam generator, wherein the heat source of said heat recovery steam generator consists of the exhaust gases of said gas turbine, and wherein at least one steam flow produced by said heat recovery steam generator is used as a heat source for at least one component of said plant, preferably for the synthesis loop stripper.

The method of revamping is applicable in particular to older urea plants of the conventional type, without strippers, for example plants known as "total recycle" plants, as well as more modern plants which perform stripping of the reactor effluent, in particular $CO_2$ stripping plants.

These and other advantages will become clear from the detailed description below, with reference to FIG. 1 which schematically illustrates a preferred embodiment of the invention.

DETAILED DESCRIPTION

FIG. 1 illustrates schematically a urea synthesis loop 1 which comprises a reactor 2, a stripper 3, a condenser 4 and a scrubber 31. The synthesis loop 1 is supplied with ammonia 5 and carbon dioxide 6.

Said loop 1 is well-known to the person skilled in the art and does not need to be described in detail. The example relates to a $CO_2$-stripping plant in which the ammonia 5 is supplied to the condenser 4 and the carbon dioxide 6 is supplied to the stripper 3; in other embodiments the ammonia and the $CO_2$ may be supplied to other points of the plant. The aqueous urea-containing solution 20 leaving the reactor 2 is concentrated in the stripper 3 and the solution 21 leaving the stripper is further treated in a recovery section using a technique known per se.

The stripper 3 is heated by steam at about 20 bar, entering via line 7 and exiting via line 8. The condenser 4 releases heat, producing a flow of steam 9 at a low pressure, for example 3 bar.

The components of the loop 1 operate at a predefined high pressure, which substantially is the same for the reactor 2, the stripper 3 and the condenser 4.

The carbon dioxide 6 is raised to said pressure of the loop 1 by a compressor 10. Said compressor is driven mechanically by a gas turbine unit 11 which essentially comprises an air compressor 12, a combustor 13 and a turbine 14. For example, and preferably, the $CO_2$ compressor 10 is mounted on the shaft of said turbine 14. The gas turbine unit is fed with a fuel 15, for example natural gas or a suitable synthesis gas.

The exhaust gases 16 of the gas turbine 14, which are at a high temperature, are conveyed to a heat recovery steam generator (HRSG) 17. Said generator 17 produces the steam 7 intended to supply heat to the stripper. In particular, said steam 7 is obtained by heating feed water 30 previously degassed inside a degasser 19; said degasser 19 is heated by steam 9 produced in the condenser 4 of the loop 1. The line 22 indicates the cooled gases leaving the generator 17.

Usually the steam production in the condenser 4 exceeds the requirement of the degasser 19, therefore the steam 9 which supplies the degasser 19 may be a fraction of the steam which is actually produced. The remaining part 9' of the steam may be used by other users of the plant or exported. Moreover, part of the steam 7 may also be destined for other plant users or exported, as indicated by the line 7'.

As can be understood from the figure, in this way high efficiency and good integration between the steam system and the urea plant are achieved. The fuel 15 in fact provides both the mechanical work of the compressor 10 and the heat for the stripper 3, owing to the efficient use in the turbine-recovery steam generator assembly; the invention also ensures optimum use of the steam 9 with a low energy level.

The invention claimed is:

1. A plant for the synthesis of urea, comprising:
    a synthesis section comprising at least one reactor,
    a compressor feeding $CO_2$ to said synthesis section,
    characterized in that it comprises a gas turbine for the operation of said $CO_2$ compressor and in that it comprises a heat recovery steam generator,
    wherein a hot source of said heat recovery steam generator is represented by exhaust gases of said gas turbine,
    and wherein at least one steam flow produced by said heat recovery steam generator is used as heat source for at least one component of said urea plant.

2. The plant according to claim 1, wherein said gas turbine directly drives said $CO_2$ compressor.

3. The plant according to claim 1, wherein the synthesis section also comprises at least one stripper and a condenser, and wherein a steam flow produced by said heat recovery steam generator is used as heating fluid for said stripper.

4. The plant according to claim 3, wherein said heat recovery steam generator produces a flow of saturated steam at a pressure of between 10 and 30 bar and said saturated steam is supplied to said at least one stripper of the synthesis section as heating fluid.

5. The plant according to claim 3, wherein:
    the plant comprises a degasser which produces a flow of demineralized water,
    said degasser is supplied with steam obtained from cooling of said condenser of the synthesis section, and
    said heat recovery steam generator is supplied with demineralized water produced in said degasser.

6. The plant according to claim 5, wherein said steam which supplies the degasser has a pressure lower than 6 bar relative.

7. A method for revamping a plant for the synthesis of urea from ammonia and $CO_2$, wherein:
- the plant includes a synthesis section, operating at a predefined synthesis pressure, comprising at least one reactor,
- the plant also comprises a $CO_2$ compressor for feeding $CO_2$ to at least one of the components of said synthesis section;
- the method being characterized by the additional installation of a gas turbine for the operation of said $CO_2$ compressor,
- and the additional installation of a heat recovery steam generator, wherein a heat source of said heat recovery steam generator is represented by the exhaust gases of said gas turbine, and wherein at least one steam flow produced by said heat recovery steam generator is used as heat source for at least one component of said plant.

8. The method according to claim 7, wherein the synthesis section comprises a stripper and a condenser, and the method envisages that a steam flow produced by said heat recovery steam generator is used as heat source for the stripper of the synthesis section.

9. The plant according to claim 4, wherein said heat recovery steam generator produces a flow of saturated steam at a pressure of about 20 bar.

10. The plant according to claim 6, wherein said steam which supplies the degasser has a pressure of about 3 bar relative.

\* \* \* \* \*